United States Patent
Azzam et al.

(10) Patent No.: US 6,620,101 B2
(45) Date of Patent: Sep. 16, 2003

(54) BONE MEASUREMENT DEVICE

(75) Inventors: Najed H. Azzam, Nazareth (IL); Samer M. Srouji, Nazareth (IL)

(73) Assignee: Dentosonic Ltd., Nesher (IL)

( * ) Notice: Subject to any disclaimer, the term of this patent is extended or adjusted under 35 U.S.C. 154(b) by 0 days.

(21) Appl. No.: 09/912,420

(22) Filed: Jul. 26, 2001

(65) Prior Publication Data

US 2003/0023167 A1 Jan. 30, 2003

(51) Int. Cl.7 .................................................. A61B 8/00
(52) U.S. Cl. ........................................ 600/439; 600/443
(58) Field of Search ............................... 600/437, 438, 600/439, 443, 447, 449; 433/2, 27, 29, 72, 86, 215

(56) References Cited

U.S. PATENT DOCUMENTS

| 4,421,119 A | | 12/1983 | Pratt, Jr. | |
| 4,722,345 A | * | 2/1988 | Ueno et al. | 600/443 |
| 4,941,474 A | * | 7/1990 | Pratt, Jr. | 600/449 |
| 5,115,813 A | * | 5/1992 | Ylander et al. | 600/437 |
| 6,030,221 A | * | 2/2000 | Jones et al. | 433/215 |
| 6,221,019 B1 | | 4/2001 | Kantorovich | |

FOREIGN PATENT DOCUMENTS

| DE | 42 05 360 A1 | 8/1993 |
| DE | 199 21 279 C1 | 11/2000 |
| EP | 0 353 209 A1 | 1/1990 |
| WO | 01 00102 | 1/2001 |

* cited by examiner

*Primary Examiner*—Francis J. Jaworski
(74) *Attorney, Agent, or Firm*—Browdy and Neimark, P.L.L.C.

(57) ABSTRACT

The invention relates to a measurement device for use in treatment of a patient's bone, containing a specific location, which is of the kind reflecting ultrasonic radiation and which is to be prevented from being contacted during the treatment. The measurement device comprises two ultrasound probes that are to be located at opposite sides of the bone. Both probes are capable of receiving the reflected ultrasonic radiation, at least one of the probes being a transceiver. The two probes are operable to communicate with each other to generate measured data indicative of a relative position of said location in the bone with respect to the probes. The invention also relates to a measurement device for use in dental treatment of a patient's alveolar bone that contains a nerve canal. The measurement device comprises a plurality of transceivers arranged in two arrays supported with adjustable distance between them so as to be placed at opposite sides of the bone, respectively, inside the patient's mouth. The transceiver arrays are selectively operated, such that one array transmits ultrasonic radiation towards the other array through the bone, and receives reflections of said ultrasonic radiation. This enables three-dimensional imaging of a region between the transceiver arrays and enables the location of the nerve canal.

16 Claims, 4 Drawing Sheets

BONE MEASUREMENT DEVICE

FIELD OF THE INVENTION

This invention is in the field of ultrasound based measurement techniques, and relates to a measurement method and device for determining a specific location in a patient's bone, particularly useful for facilitating dental treatment by determining an appropriate drilling depth.

BACKGROUND OF THE INVENTION

It is a typical dental procedure to use endosseous osseointegrated root for implants for tooth replacement in the posterior Audible. This process requires the drilling of an implant-receiving cavity. Before commencing the drilling, an investigation is made to determine the length of the longest physiologically possible implant which can be safely implanted whilst leaving sufficient alveolar bone tissue (typically of about 2 mm) above the superior border of the mandibular canal in the posterior mandible, through which the plexus of nerves extends. A term "nerve canal" will be used herein to refer to a specific location of which contact, such as by drilling, is to be avoided. The mandibular canal of the posterior mandible is one example. In the case when the nerve canal includes nerves, contact often results in the undesired perforation thereof.

Known dental techniques for determining the length of the longest physiologically possible implant utilize panoramic X-ray radiography or CT scans. To avoid the possible puncture of the mandibular canal, implants shorter than those that are physiologically safe are typically performed. Such implants, however, suffer from reduced osseointegration with the surrounding bone tissue and are therefore less successful.

It is also important that the condition of the posterior mandible and the posterior maxilla be assessed prior to drilling an implant receiving cavity, in order to determine whether the bone is suitable for receiving an implant and to avoid unnecessary surgical performance. Such an assessment may be carried out by examining the porosity of the bone tissue.

WO 01/00102, assigned to the assignee of the present application, discloses an ultrasound-based technique for achieving the above purposes. According to this technique, a single ultrasonic probe is applied to the patient's jaw from the interior of the patient's mouth.

SUMMARY OF THE INVENTION

There is accordingly a need in the art to facilitate the location of a nerve canal in a patient's bone to thereby facilitate treatment, such as dental procedures, aimed at drilling a cavity in bone, by providing a novel measurement system and method.

The present invention utilizes an ultrasound-based measurement technique, and provides for locating a nerve canal in the bone. Considering a dental treatment, the present invention allows for determining the length of the longest physiologically possible implant defining a drilling depth. This can be implemented either by utilizing ultrasound measurements and a preliminary drilling procedure, prior to starting the implant drilling, or by taking ultrasound measurements that enable three-dimensional imaging of the patient's bone. Additionally, the invention provides for determining the velocity of sound propagation through the bone tissue that is indicative of the porous condition thereof.

Generally, the present invention can assist in any treatment of the kind in which preventing a specific location in the bone from being contacted during the treatment is desired.

The main idea of the present invention consists of using two ultrasonic probes, wherein at least one of the probes is operable as a transceiver, and the other may be a receiver or a transceiver. The probes are applied at opposite sides of the bone which is to be treated, and operate together to measure the distance between the receiver and a nerve canal in the bone at two different states of the bone, respectively, prior to and after the bone has undergone a certain preliminary drilling. By this, an optimal drilling preventing the nerve canal from being contacted can be determined.

Thus according to one broad aspect of the present invention, there is provided a measurement device for use in treatment of a patient's bone, containing a specific location, which is of the kind reflecting ultrasonic radiation and which is to be prevented from being contacted during the treatment, the measurement device comprising:

(i) two ultrasound probes that are to be located at opposite sides of the bone, at least one of the probes being a transceiver, the two probes being operable to communicate with each other to generate measured data indicative of a relative position of said location in the bone with respect to the probes; and (ii) an electronic assembly connectable to the probes, so as to selectively operate each of them, and to be responsive to the measured data to thereby enable the determination of said relative position.

According to one embodiment of the invention, the transceiver and receiver are used to measure the distances between the receiver and the specific location in the bone at two different states of the bone, respectively, prior to and after the bone has undergone a certain preliminary drilling. By this, an optimal drilling depth preventing the specific location from being contacted can be determined. According to another embodiment of the invention, the probes are two arrays, respectively, of ultrasound transceivers, enabling three-dimensional imaging of the bone including the nerve canal.

Thus according to another broad aspect of the present invention, there is provided a measurement device for use in treatment of a patient's bone including a drilling of the bone, wherein the bone contains a specific location of the kind reflecting ultrasonic radiation which is to be prevented from being contacted during the drilling, the measurement device comprising:

(a) a first ultrasonic probe for applying to said bone from one side thereof, the first probe being a transceiver operable to transmit ultrasound radiation. through the bone, to receive the ultrasound radiation returned from said location within the bone, and to generate first measured data representative of the received radiation, said first data being indicative of a location of the transceiver with respect to said location in the bone and indicative of a distance between the transceiver and said location;

(b) a second ultrasonic probe for applying to sad bone at the opposite side thereof, the second probe being a receiver operable to receive the ultrasound radiation transmitted by said transceiver through the bone, and to generate second measured data representative of the radiation received by the receiver; said second data being indicative of a relative location of the receiver with respect to the transceiver and indicative of a distance between the receiver and the transceiver; and (c) an electronic assembly associated with the transceiver and to the receiver, so as to selectively operate each of them, and to be responsive to the measured data to thereby enable desired positioning of the transceiver and the receiver, and enable the determination of a relative position of said location in the bone with respect to the receiver to be used for determining and optimal drilling depth preventing said location from being contacted.

More specifically, the present invention is used in dental treatments including drilling of a patient's alveolar bone. To this end, two ultrasonic probes are applied to the opposite sides of the patient's jaw, respectively. One of the probes may be applied from the interior and the other from the exterior of the patient's mouth. The external probe is operable as a transceiver, and the internal probe is operable as a receiver. The independent operation of the transceiver enables its desired positioning with respect to the nerve canal within the jaw. When the transceiver is fixed in the desired location, the receiver is put into operation at the opposite side of the jaw to detect signals transmitted by the transceiver, in order to provide a desired positioning of the receiver with respect to the transceiver. Then, a measurement session is performed by both probes consisting of at least two time of flight measurements, wherein one measurement is taken prior to a preliminary drilling of a preset depth, and the other is taken thereafter.

Both probes may be applied to opposite sides of the bone from the interior of the patient's mouth. In this case, the probes are arrays of transceivers, and are sequentially operated to create a three-dimensional image of the bone including the nerve canal, which image is then used for guiding the bone treatment.

Thus, according to yet another broad aspect of the present invention, there is provided a measurement device, which is to be used in dental treatment including a drilling of a patient's alveolar bone, the measurement device comprising:

(a) a fist ultrasonic probe for applying to the patient's jaw from the exterior of the patient's mouth, the first probe being a transceiver operable to transmit ultrasound radiation through the alveolar bone, to receive the ultrasound radiation returned from a nerve canal within the bone, and generate first measured data representative of the received radiation, said first data being indicative of a relative location of the transceiver with respect to the nerve canal thereby enabling a desired positioning of the transceiver, and indicative of a distance between the transceiver and said nerve canal;

(b) a second ultrasonic probe for applying to the patient's jaw from the interior of the patient's mouth, the second probe being a receiver operable to detect the ultrasound radiation transmitted by said transceiver through the bone, and to generate second measured data representative of the radiation received by the receiver, said second data being indicative of a relative location of the receiver with respect to the transceiver, thereby enabling a desired positioning of the receiver, and indicative of a distance between the receiver and the transceiver; and (c) all electronic assembly associated with the transceiver and the receiver to analyze the measured data to enable said desired positioning of the transceiver and the receiver, and enable the determination of a distance between the receiver and the nerve canal to be used for determining and optimal drilling depth.

According to yet another aspect of the present invention, there is provided a dental treatment system comprising an ultrasonic measurement device associated with a drilling tool for drilling a cavity in a patient's alveolar bone, wherein:

the measurement device comprises:
two ultrasound probes that are to be located at opposite sides of the bones at least one of the probes being a transceiver, the two probes being operable to communicate with each other to generate measured data indicative of a relative position of said location in the bone with respect to the probes; and an electronic assembly associated with the probes, so as to selectively operate each of them, and to be responsive to the measured data to enable the determination of said relative position, and thereby the determination of an optimal drilling depth;

the system is operable to activate the measurement device to take measurements and utilize the measured data to guide the drilling tool.

BRIEF DESCRIPTION OF THE DRAWINGS

In order to understand the invention and to see how it may be carried out in practice, a preferred embodiment will now be described, by way of non-voting limiting example only, with reference to the accompanying drawings, in which.

DETAILED DESCRIPTION OF THE INVENTION

Specifically the present invention is useful in facilitating the treatment of a patient's alveolar bone, and is therefore described below with respect to this application.

Figure 1:
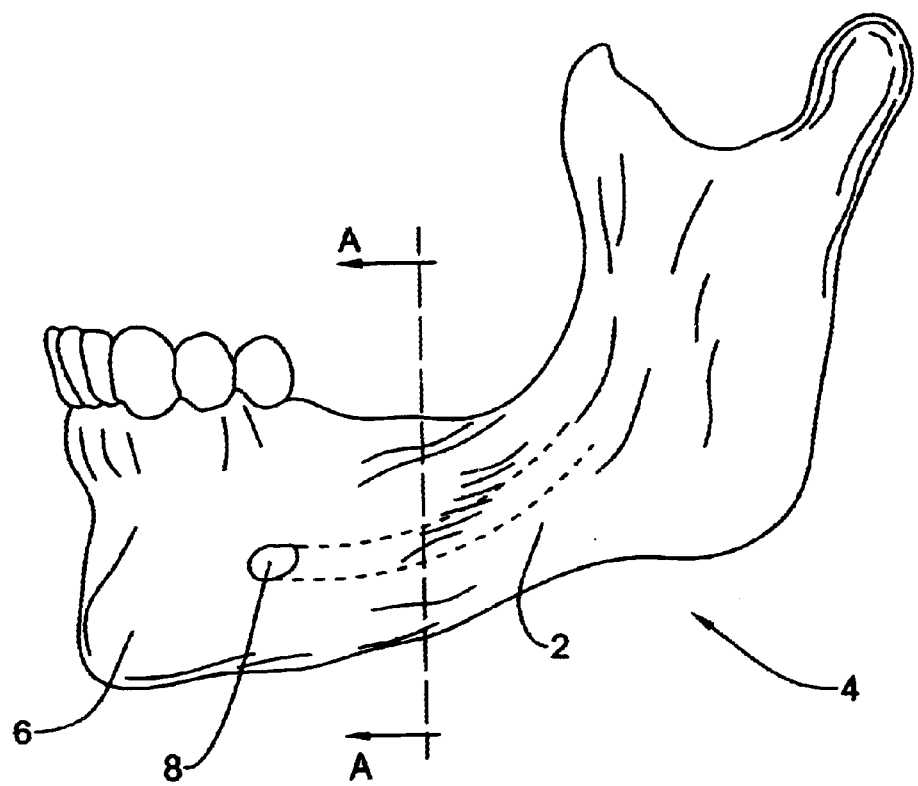
FIG. 1 is a perspective view of the posterior mandible of a human subject's lower jaw, for which the present invention may be used.

FIG. 1 shows the alveolar bone 2 of the posterior mandible 4 of a patient's lower jaw 6 and the nerve canal 8, which longitudinally extends within the bone 2. In order to enable successful drilling and consequent placing of a lasting implant in the jaw 6, it is important that drilling and implantation are as deep as physiologically possible, but avoid contacting the nerve canal 8.

Figure 2:
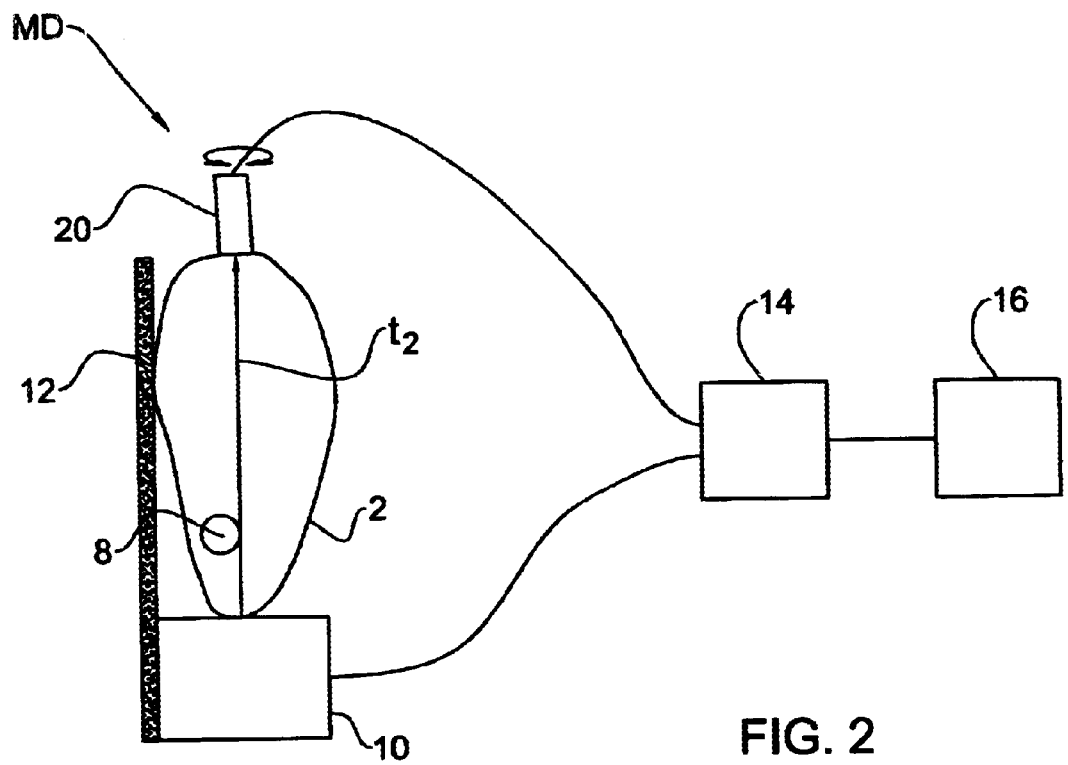
FIG. 2 schematically illustrates the main components of the device according to the invention as applied to a patient's jaw.

FIG. 2 shows a measurement device MD according to the present invention as it is used for determining the optimal, safe drilling depth of the longest physiologically possible cavity for a dental implant. The device MD comprises such main constructional parts as an ultrasonic transceiver 10 for applying either directly to the skin tissue (not shown) that covers the alveolar bone 2 (shown here in cross-section taken from axis A—A in FIG. 1) or indirectly via an intermediary ultrasonic transmission medium (not shown) such as a disposable silicone sleeve. The device MD further comprises an ultrasonic receiver 20 capable of receiving ultrasonic pulses transmitted by the transceiver 10, and both the transceiver 10 and the receiver 20 are associated with an electronic assembly 14. The latter selectively operates the transceiver and receiver 10 and 20, and processes signals received therefrom. The electronic assembly 14 may be part of a control unit (typically a computer) having an LCD monitor 16 to interpret the processed signals and to display an image of the cross section of the jaw. The transceiver and receiver 10 and 20 may include tracking sensors (not shown) to locate their relative position and display it on the monitor 16.

Figure 3A:
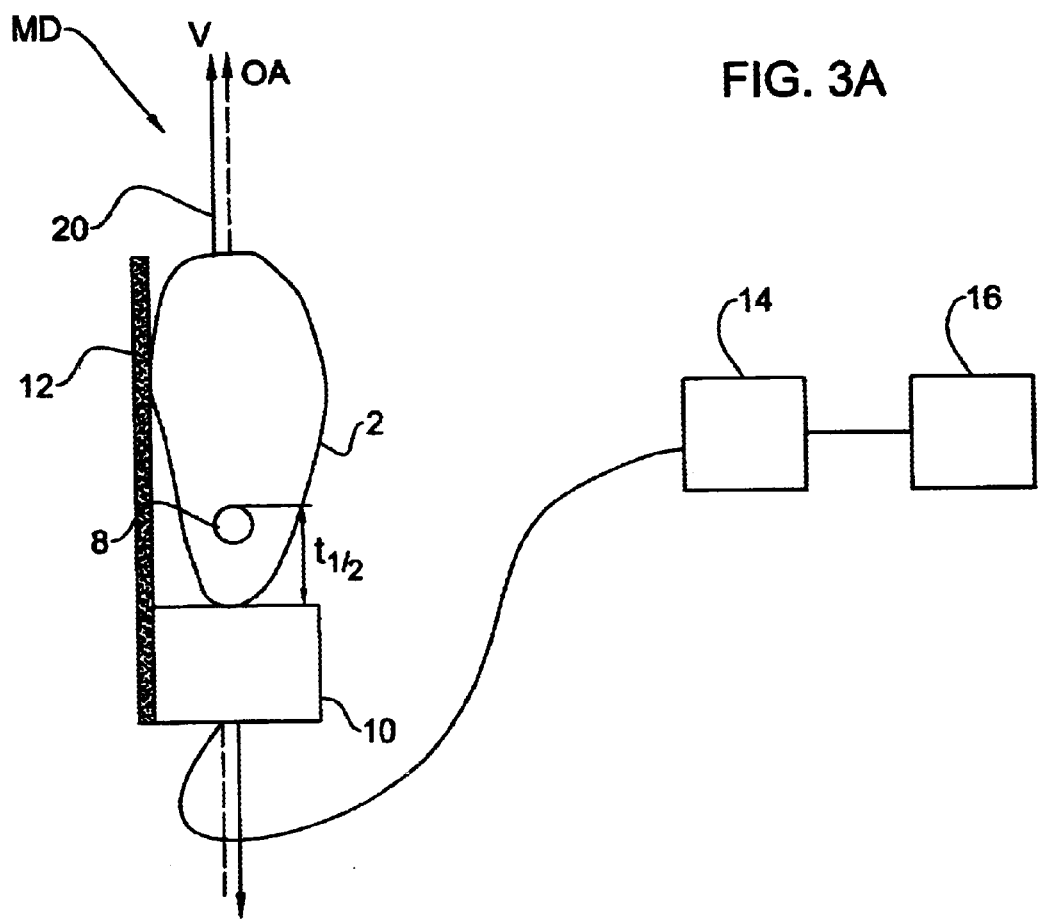
FIG. 3A illustrates an initial measurement stage in the operation of the device of FIG. 2.

The measurement device MD is used in a dental treatment system including a drilling tool (which is not shown) for performing a preliminary drilling of the bone. The operation of the device MD will now be described with reference to FIGS. 2, 3A–3C and 4. FIG. 3A illustrates an initial measurement stage in the operation of the device. As shown, the transceiver 10 is equipped with a fixation tool 12 that serves to maintain the transceiver 10 in a desired position, which may be displayed on the monitor 16. The fixation tool 12 carries tracking sensors (not shown) to track the location and movement of the transducer 20 or the drilling tool (not shown) inside the mouth. Generally, the tracking sensors may be of any known kind and therefore need not be specifically described except to note the following.

Figure 3B:
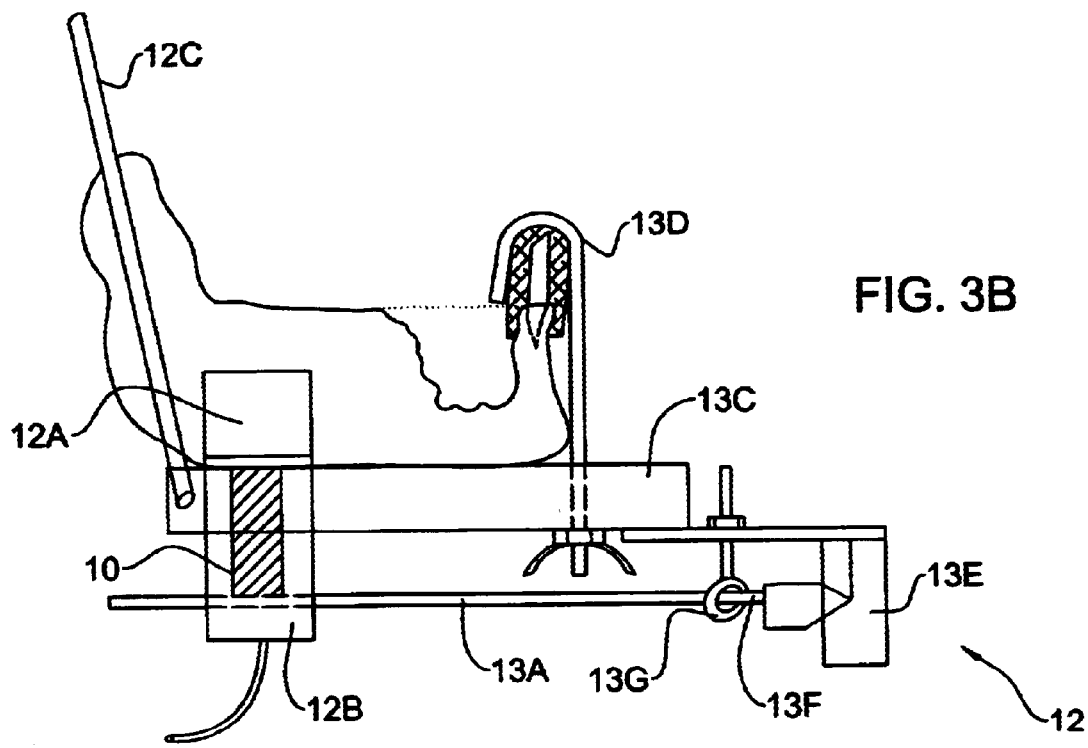
FIGS. 3B and 3C illustrate more specifically a fixation tool suitable for use in the present invention.
Figure 3C:
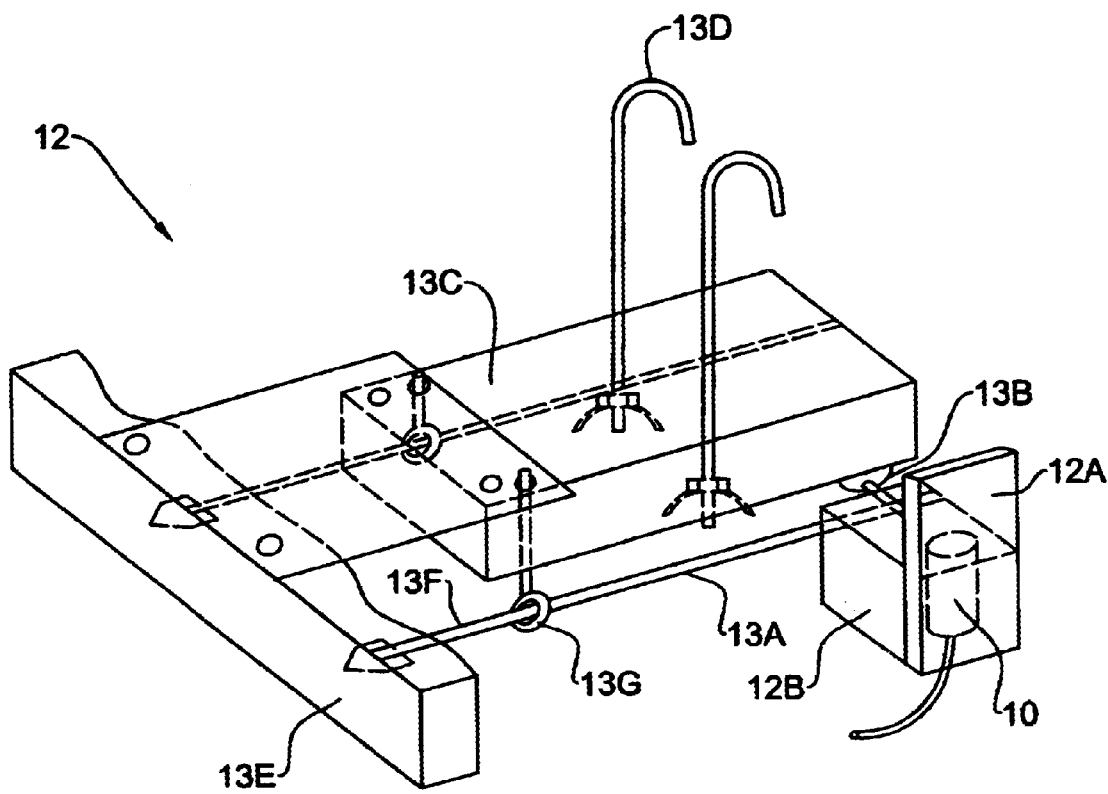

As shown in FIGS. 3B and 3C, the fixation tool 12 comprises such main constructional parts as two support members 12A and 12B carrying, respectively, tracking sensors (not shown) and the transceiver 10. The fixation tool 12 may be attached to the patient's jaw by at least one attachment member 12C, such as a strap to encircle the patient's head. The support members 12A and 12B are mounted for sliding movement along an axis of a rod-like member 13A. The support members (constituting a probe holder) are fixed in place by an adjustable locking mechanism 13B and a support base 13C that is to be located under the chin and to be attached to a patient's jaw, for example by means of hooks 13D. The rod 13A is, in turn, is attached to a holding plate 13E through a connecting member 13F, and is mounted for rotation with respect to the connecting member 13F, by means of a suitable mechanism 13G allowing three degrees of freedom (e.g., ball-and-socket mechanism). Thus, the fixation tool is designed so as to provide reciprocating and rotation of the probe holder (members 12A and 12B) with respect to the axis of the rod 13A.

At an initial measurement stage, the transceiver 10 is calibrated in a conventional manner and applied to the lower jaw 6 exterior to the patient's mouth (not shown). Then, the transceiver 10 is put in operation to transmit and receive ultrasonic echo pulses towards and from the bone 2 (through the jaw 6), and generate output signals indicative of the received pulses. These signals are processed by the assembly 14, and an image of the cross-section of the patient's lower jaw 6 appears on the LCD monitor 16. Additional information that may be displayed (due to the provision of the tracking sensor) includes an indication of the location of the transceiver 10 on this cross-section. The transceiver 10 is manipulated on the surface of the jaw 6 to provide the desired position thereof with respect to an axis OA of the jaw 6 passing through the nerve canal 8, namely, such that the transceiver 10 is aligned with the axis OA, being thereby capable of detecting signals reflected from the nerve canal 8. To this end, the amplitudes of the returning pulses are analyzed by the electronic assembly 14, until the maximum thereof is detected. This maximum corresponds to the desired position for the transceiver 10 (constituting a first desired position) directly below the nerve canal 8. The transceiver 10 is fixed in place at this position using the fixation tool 12.

The displayed orientation of the image of the cross-section of the patient's lower jaw 6 may also be varied (due to the provision of the tracking sensor) in such a way, for example, as to display the image of the cross-section making an angle with a predetermined vertical axis V that is equal to the angle between the axis V and the axis OA.

A time of flight $t_1$ for the pulse corresponding to the maximum amplitude is measured for the purposes of the invention. This measurement (constituting a first measured data) can be taken during the positioning stage, or thereafter, when the transceiver has been fixed in the desired position. An ultrasonic pulse echo is transmitted from his position to the nerve canal 8, which reflects the pulse back to be received by the transceiver 10. The time of flight $t_1$ of the pulse is measured and recorded for use in the further data analysis. It should be understood that the time of flight $t_1$, corresponds to the time necessary for the ultrasonic signal to traverse twice the distance between the transceiver 10 and the nerve canal 8. This time $t_1$ is proportional to the distance traversed by the ultrasound pulse between the transceiver and the nerve canal.

Turning back to FIG. 2, at an intermediate measurement stage, the receiver 20 is applied to the lower jaw 6 on the interior of the mouth at a site at which a drilled cavity is needed for a dental implant. This stage is aimed at both measuring and providing a desired position of the receiver with respect to the transceiver (constituting a second desired position). The transceiver 10 and receiver 20 are both calibrated, and the transceiver 10 is operated by the electronic assembly to transmit ultrasonic pulses, which are received by the receiver 20. The latter generates signals indicative of the received pulses, and a cross-sectional image of the patient's lower jaw 6 is displayed on the LCD monitor 16. The receiver 20 is then manipulated about the drilling site on the surface of the lower jaw 6 and the tracking sensors track the position of the receiver 20, as the amplitudes of the transmitted pulses are analyzed by the electronic assembly 14 until the maximum amplitude is detected. This maximum corresponds to the desired relative position for the receiver 20, namely, the received pulse of the maximal amplitude is not obstructed by the nerve canal 8. The monitor 16, which displays a cross sectional image of the jaw, also displays a guiding line from the location of the receiver 20 as tracked by the tracking sensors along the direction of the maximum amplitude. The guiding line is stored by the electronic assembly 14 to be subsequently used to indicate the drilling path. A time of flight $t_2$ for the pulse corresponding to the maximum amplitude is measured (constituting a list portion of a second measured data) either during this positioning stage, or thereafter, the receiver being maintained in the desired position. This tine $t_2$ is proportional to the distance traversed by the ultrasound pulse between the transceiver and receiver 10 and 20.

Thereafter, a preliminary drilling of a preset depth D in the bone 2 is performed at a location corresponding to the desired position of the receiver. To this end, a drilling tool of about 3.2 mm diameter is used. The drilling tool is tracked by the tracking sensors on the fixation tool 12 during drilling, and its position and projected path are displayed on the monitor 16. The guiding line is also displayed to indicate the preferred location and direction of drilling. The monitor 16 may also display the accuracy of drilling by indicating to what extent drilling is achieved along the guiding line. For example, the guiding line may be displayed in one color, the projected path in another color, and their overlapping in yet another color to indicate drilling along the desired path.

Figure 4:
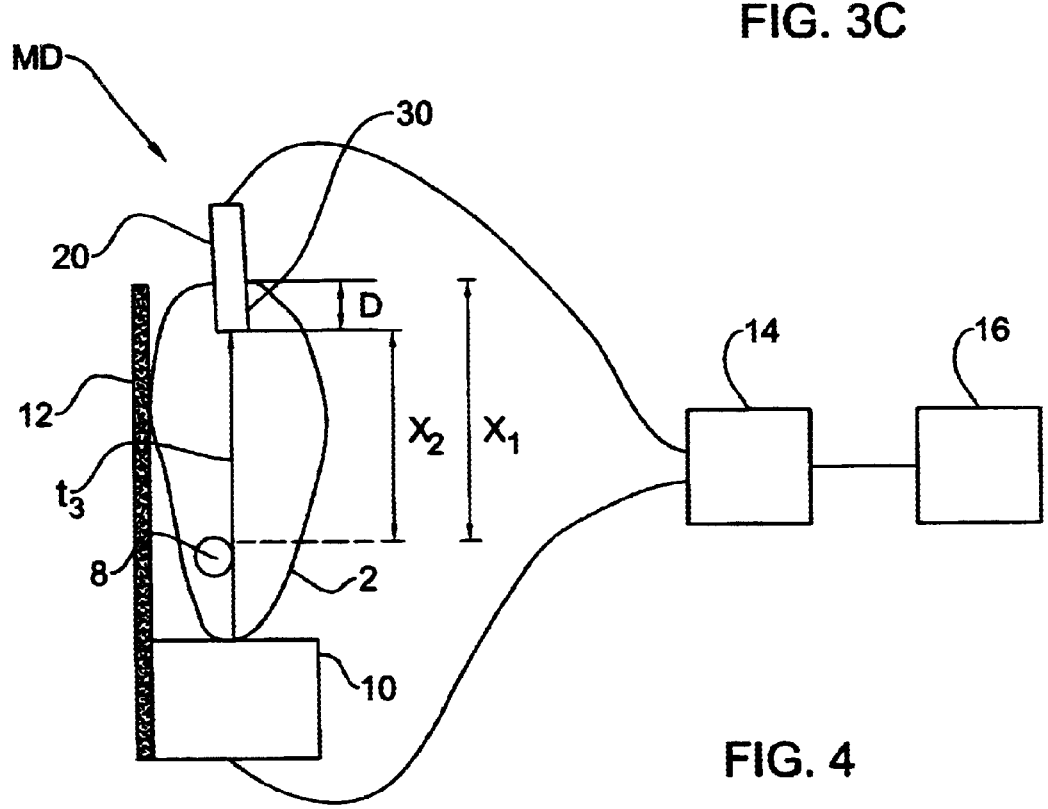
FIG. 4 illustrates a final measurement stage in the operation of the device of FIG. 2.

FIG. 4 shows the device MD as it is used at a subsequent final measurement stage. As shown, the receiver 20 is inserted into a cavity 30 having a depth D resulting from the preliminary drilling, until the receiver abuts the cavity's base. The transceiver 10 and receiver 20 are then operated to respectively, transmit and receive the ultrasonic pulse. The receiver 20 generates data indicative of the received pulse, a time of flight $t_3$ of the received pulse is measured (constituting a second portion of the second measured data). This time $t_3$ is indicative of the distance traversed by the ultrasound pulse between the transceiver and receiver through the bone in the preliminary drilled state thereof.

Thus, taking into account the known depth D and considering the time of flights $t_1$, $t_2$ and $t_3$, the relevant distances $X_1$ and $X_2$, corresponding to the distances between the nerve canal 8 and the receiver 20 at, respectively, the initial state of the bone (prior to preliminary drilling) and the drilled state (preliminary drilling), can be calculated as follows:

$$X_1 = V(t_2 - t_1/2) \quad (1)$$

$$X_2 = V(t_3 - t_1/2) \quad (2)$$

Since the difference between $X_1$ and $X_2$ is equal to the preliminary drilling depth D, the velocity V of sound propagation in the bone 2 can be determined:

$$D = X_1 - X_2 = V(t_2 - t_3) \quad (3)$$

$$V = D/(t_2 - t_3) \quad (4)$$

By this, the distances $X_1$ and $X_2$ can be calculated, and the determined value of the sound velocity V can be used for the estimation of the porous condition of a given patient's bone indicative of the bone density by comparing it to a known reference database. Deviations from values in this database, for example, may indicate an imperfection in the bone and, in general, may aid in deciding whether treatment of the bone should take place.

These calculations are carried out by an appropriate utility of the electronic assembly 14, and displayed on the LCD monitor 16. By knowing the distances $X_1$ and $X_2$, the nerve canal 8 can be precisely located and the optimal drilling depth of the longest physiologically possible cavity for a dental implant can be accordingly determined.

Removable sleeves of an ultrasound transmission media may be fitted on the transceiver 10 and the receiver 20 to facilitate propagation of the ultrasonic waves. The sleeves, which may be easily cleaned, also serve to maintain a higher degree of hygiene, keeping, for example, the transceiver 10 and the receiver 20 from directly contacting the patient. The sleeves may be disposable or reusable.

Figure 5A:
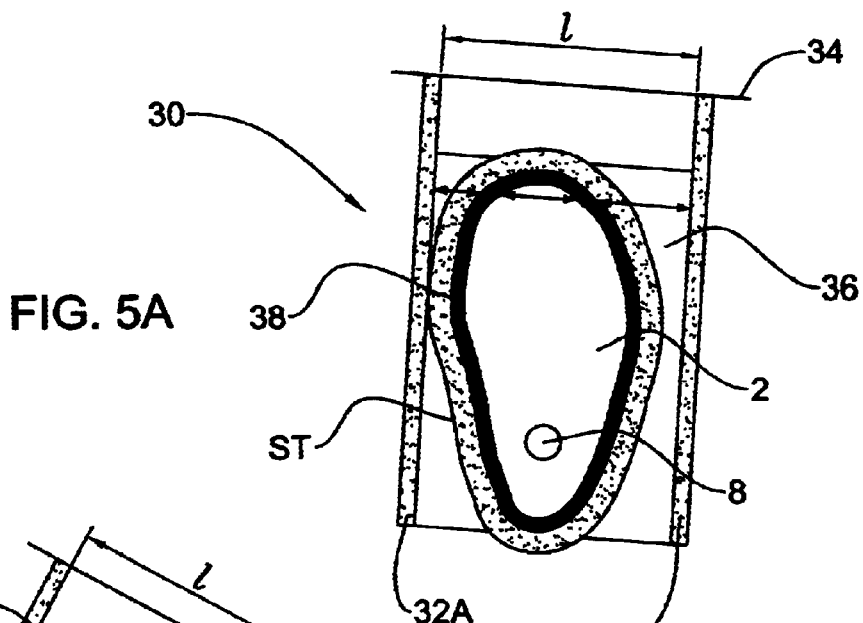
FIGS. 5A to 5C illustrate an imaging device according to the present invention.
Figure 5B:
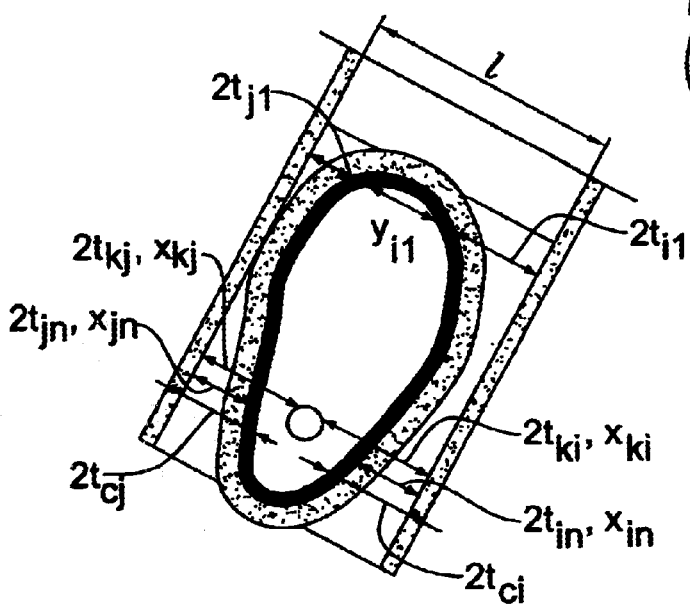
Figure 5C:
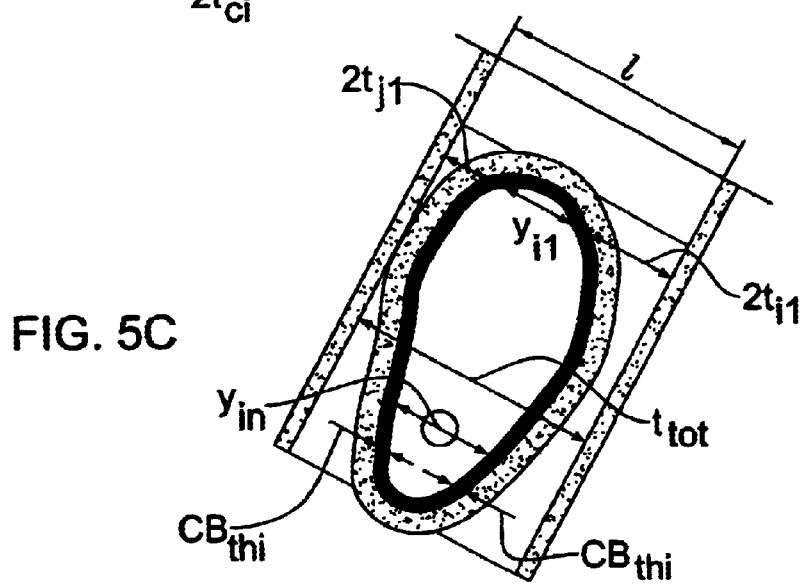

Turning now to FIGS. 5A–5C, there is illustrated a measurement device 30 constructed and operated according to another embodiment of the invention and used with the alveolar bone 2 (shown here, as in previous figures, in a cross-section taken from axis A—A in FIG. 1). The device 30 is composed of two ultrasound probes 32A and 32B supported by a connecting element 34 and designed to be placed inside the patient's mouth at opposite sides of the bone. Each probe is a matrix (one- or two-dimensional array) of ultrasound transceivers, the device 30 thereby acting as an imaging device, each ultrasound transceiver presenting a pixel in the obtained image. The probes 32A and 32B are mounted for sliding movement along the connecting element 34, which thereby keeps the probes parallel and maintains a desired distance l between the probes 32A and 32B. This may be facilitated by the use of springs to hold the probes against the tension of the springs, when at the desired distance between the probes. The distance l may be immediately determined by having markings on the device 30 to indicate the length between the probes 32A and 32B as they slide away from each other. This may also be done electronically.

The device 30 further comprises a contacting disposable element 36, which is, at its one side, attached to the probes 32A and 32B, and, at its free side, intended for contacting the soft tissue surrounding the bone 2. The element 36 is made of a suitable flexible ultrasonic transmission material, which may have an acoustic impedance similar to that of the soft tissue ST surrounding the bone. This may for example, be silicone.

Sequential operation of the probes 32A and 32B as transceivers (with very short time intervals) enables to calculate the distance between each point (pixel) of the probe and the respective location on a bone envelope 38 (its side facing the probe). By this, a three-dimensional image of the bone 2 with its envelope 38, which is made of compact bone having a thickness $CB_{thi}$, and the nerve canal 8 within the bone 2 can be obtained. This is implemented in the following manner.

The sound velocity in the soft tissue ST and in the disposable contacting element 36 is known. Each pixel (cell) of the probe transmits an ultrasound pulse and receives its echo (reflection from the envelope 38), and respective times of flight are measured. Considering the ij-matrices, times of fights 2tj1 and 2ti1 are sequentially measured for all pixels in the probes, and distances Xj1 and Xi1 are calculated as follows:

$$X_{j1} = V_{st} \cdot t_{j1} \quad (5)$$

and $$X_{i1} = V_{st} \cdot t_{i1} \quad (6)$$

Since the current distance l is known, the thickness of the bone 2 at each point (with respect to each pixel) is equal to: $Y_i = l - X_j - X_i$. Having measured the bone thickness at various heights of the probe, the electronic assembly (not shown here) can, present the exact envelope 38 of the bone within the measured area. Any cross section of the full three-dimensional image can then be presented (by using suitable software).

The imaging of the nerve canal 8 is carried out in the following manner. From the location of the nerve canal 8, different echoes will be received (as compared to that associated with the envelope) by both probes, namely reflections from the nerve canal 8. Times of flight $2t_{kj}$ and $2t_{ki}$ will be measured at distances $X_{kj}$ and $X_{ki}$. At this location what will actually be received are three signals for each pair of pixels corresponding to (1) the reflected echoes from the outer side of the bone envelope 38 with the time flights $2t_{in}$ and $2t_{jn}$; (2) the reflected echoes from the inner side of the bone envelope 38 having times of flight $2t_{ci}$ and $2t_{cj}$; and (3) the reflected echoes from the nerve canal 8 having times of flight $2t_{ki}$ and $2t_{kj}$. As soon as the third signal is received, the electronics is programmed to operate the opposite pixels of the probes 32A and 32B at the nerve location to operate as transmitter and receiver, respectively, to thereby determine the total time of flight $t_{tot}$ for a signal traveling between the corresponding pair of opposite pixels.

Considering the known sound velocity on the soft tissue $V_{st}$ and that in the compact bone $V_{cb}$, the perimeter of the nerve canal 8 can be imaged using the following equations:

$$X_{in} = V_{st} \cdot t_{in} \quad (7)$$

$$CB_{thi} = V_{cb} \cdot (t_{ci} - t_{in}) \quad (8)$$

Similar calculations are performed for the other probe, namely:

$$X_{jn} = V_{si} \cdot t_{jn} \quad (9)$$

$$CB'_{thi} = V_{cb} \cdot (t_{cj} - t_{jn}) \quad (10)$$

Hence, the thickness $Y_{in}$ of the bone at the current location (respective pixels) can be determined as follows:

$$Y_{in} = 1 - (X_{in} + CB_{thi} + X_{jn} + CB'_{thi}) \quad (11)$$

Owing to the fact that the sound velocity within the compact bone is known, the following equation can be written:

$$V_{cb} = Y_{in}/(t_{tot} - t_{ci} - t_{cj}) \quad (12)$$

Therefore, the distance between each point of the nerve canal perimeter and the respective pixel of the probe is as follows:

$$X_{ki} V_{cb} \cdot (t_{ki} - t_{ci}) + X_{in} + CB_{thi} \quad (12)$$

$$X_{kj} = V_{cb} \cdot (t_{kj} - t_{cj}) + X_{jn} + CB'_{thi} \quad (13)$$

Using the above information, the electronics can construct a three-dimensional image for the measured section of the jaw 6 and the nerve canal 8, which is displayed on the monitor.

It should be noted, although not specifically shown, that the device 30 is used with a system of tracking sensors (not shown), which is to be mounted outside the patient's mouth from the cheek side and fixed on the jaw. The tracking sensors will be registered with the location of the probes 32A and 32B inside the mouth, and the three-dimensional image created by the probes. The drilling tool is equipped with an additional tracking sensor to communicate with the tracking sensors of the measurement device. In this way, the probes 32A and 32B can be removed from the mouth after the three-dimensional image of the measured section of the jaw 6 and the nerve canal 8 is created, while maintaining the drilling tool in a proper relative position with respect to the image and keeping the drilling tool correlated with the displayed image of the respective section of the jaw.

It is thus understood, that once the three-dimensional image is created in the above-described manner, a dentist may select a specific cross section of the image intended for drilling. Therefore, the dentist can plan the number, length and location of implants, and the best drilling angle to accommodate the longest suitable implant without contacting the nerve canal. The dentist will draw a line on the monitor (using a mouse or electronic pen) to indicate the best drilling path for the selected implant. During the drilling process, the tracking sensors will follow the drilling tool movement and will transmit signals indicative of the tool location to the monitor to be seen in the image of the bone section. The dentist will align the drilling tool propagation with the drawn line. A suitable color presentation will indicate that the alignment is achieved.

The device 30 may be used for other parts of a patient's body. For example, the device 30 may be used to image the posterior mandible of the upper jaw as well, where contacting the mandibular canal is to be avoided. The posterior maxilla may also be imaged, for example, where it is preferable to avoid contacting the maxillary sinuses.

Those skilled in the art will readily appreciate that various modifications and changes can be applied to the embodiments of the invention as hereinbefore exemplified without departing from its scope defined in and by the appended claims.

What is claimed is:

1. A measurement device for use in dental treatment including a drilling of a patient's alveolar bone that contains a nerve canal which is to be prevented from being contacted during the drilling, the measurement device comprising:

(a) a first ultrasonic probe for applying to the patient's jaw from the exterior of the patient's mouth, the first probe being a transceiver operable to transmit ultrasound radiation through the alveolar bone, to receive the ultrasound radiation returned from a nerve canal within the bone, and generate first measured data representative of the received radiation, said first data being indicative of a relative location of the transceiver with respect to the nerve canal thereby enabling a desired positioning of the transceiver, and indicative of a distance between the transceiver and said nerve canal;

(b) a second ultrasonic probe for applying to the patient's jaw from the interior of the patient's mouth, the second probe being a receiver operable to detect the ultrasound radiation transmitted by said transceiver though the bone, and to generate second measured data representative of the radiation received by the receiver, said second data being indicative of a relative location of the receiver with respect to the transceiver, thereby enabling a desired positioning of the receiver; and indicative of a distance between the receiver and the transceiver; and (c) an electronic assembly associated with the transceiver and the receiver to analyze the measured data to enable said desired positioning of the transceiver and the receiver, and enable the determination of a distance between the receiver and the nerve canal to be used for determining and optimal drilling depth.

2. The device according to claim 1, wherein the desired positioning of the transceiver with respect to the nerve canal is that corresponding to a maximal intensity of the received return radiation, and the desired positioning of the receiver with respect to the transceiver is that corresponding to a maximal intensity of the transmitted radiation received by the receiver, when in the desired position of the transceiver.

3. The device according to claim 1, wherein said first measured data generated by the transceiver is indicative of a first time of flight of the ultrasonic radiation between the transmission of a pulse of the ultrasonic radiation and the receipt by the transceiver of the reflection of the pulse by the nerve canal, when the transceiver is desirably positioned.

4. The device according to claim 3, said second measured data generated by the receiver has a first data portion corresponding to a measurement taken prior to performing a preliminary drilling a preset drilling depth in the bone, and a second data portion corresponding to a measurement taken after said preliminary drilling, the receiver being located inside a drilled cavity.

5. The device according to claim 4, wherein the first and second portions of the second measured data are indicative of second and third times of flight of the transmitted ultrasonic radiation within, respectively, the non-drilled and drilled bone.

6. The device according to claim 5, wherein the distance between the receiver and the nerve canal is calculated using the known depth of the preliminary drilling.

7. The device according to claim 5, wherein the velocity of said radiation is calculated using the known depth of the preliminary drilling.

8. The device according to claim 1, wherein at least one of the first and second probes is an array of ultrasound transceiver elements selectively operable to provide measured data indicative of a three-dimensional image of the bone with the nerve canal.

9. The device according to claim 8, wherein the two probes are mounted in a manner enabling to vary a distance between the probes.

10. The device according to claim 1, further comprising a tracking sensor.

11. The device according to claim 1, further comprising a fixation tool for supporting at least the first probe that is to be located outside the patient's mouth during the measurements.

12. The device according to claim 11, wherein the fixation tool comprises a holder carrying at least said first probe and a tracking sensor, and support means for supporting the holder and allowing reciprocating and rotational movement thereof, thereby enabling to fix the first probe in a desired location with respect to the bone.

13. A dental treatment system comprising an ultrasonic measurement device associated with a drilling tool for drilling a cavity in a patient's alveolar bone that contains a nerve canal which is to be prevented from being contacted during the drilling, wherein:

the measurement device comprises:
two ultrasound probes that are to be located at opposite sides of the bone, at least one of the probes being a transceiver, the two probes being operable to communicate with each other to generate measured data indicative of a relative position of said location in the bone with respect to the probes; and
an electronic assembly connectable to the probes, so as to selectively operate each of them, and to be responsive to the measured data to enable the determination of said relative position, and thereby the determination of an optimal drilling depth;

the system is operable to activate the measurement device to take measurements and utilize the measured data to guide the drilling tool.

14. A dental treatment system comprising an ultrasonic measurement device associated with a drilling tool for drilling a cavity in a patient's alveolar bone that contains a nerve canal which is to be prevented from being contacted during the drilling, wherein:

the measurement device comprises:
first ultrasonic probe for applying to the patient's jaw from the exterior of the patient's mouth, the first probe being a transceiver operable to transmit ultrasound radiation through the alveolar bone, to receive the ultrasound radiation returned from a nerve canal within the bone, and generate first measured data representative of the received radiation, said first data being indicative of a relative location of the transceiver with respect to the nerve canal and of a distance between the transceiver and said nerve canal;
a second ultrasonic probe for applying to the patient's jaw from the interior of the patient's mouth, the second probe being a receiver operable to detect the ultrasound radiation transmitted by said transceiver though the bone, and to generate second measured data representative of the radiation received by the receiver, said second measured data being indicative of a relative location of the receiver with respect to the transceiver and of a distance between the receiver and the transceiver; and
an electronic assembly associated with the transceiver and the receiver to selectively operate them and analyze the measured data to enable desired positioning of the transceiver and the receiver, and enable the determination of a distance between the receiver and the nerve canal to be used for determining an optimal drilling depth;

the system is operable to activate the measurement device to take first and second measurements prior to operating the drilling tool for performing a preliminary drilling of a preset depth, so as to provide a desired relative positioning of the transceiver and receiver, and measure a distance between them within the bone in its non-drilled state, and to activate the measurement device to take at least one measurement after the preliminary drilling, to determine a distance between the receiver and the nerve canal when the receiver is located in a drilled cavity.

15. A dental treatment system comprising an ultrasonic measurement device associated with a drilling tool for drilling a cavity in a patient's alveolar bone that contains a nerve canal which is to be prevented from being contacted during the drilling, wherein:

the measurement device comprises a plurality of transceivers arranged in two arrays supported with adjustable distance between them so as to be placed at opposite sides of the bone, respectively, inside the patient's mouth, the transceiver arrays being selectively operated, such that one array transmits ultrasonic radiation towards the other array through the bone, and receives reflections of said ultrasonic radiation; and
an electronic assembly connectable to the measurement device, so as to selectively operate each of transceiver arrays, and to be responsive to measured data generated by the transceivers to enable the location of said nerve canal, and thereby the determination of an optimal drilling depth;

the system is operable to activate the measurement device to take measurements and utilize the measured data to guide the drilling tool.

16. The system according to claim 15, and also comprising a system of tracking sensors for locating and guiding the drilling tool.

* * * * *